United States Patent [19]

Nitsch

[11] Patent Number: 5,424,302
[45] Date of Patent: Jun. 13, 1995

[54] PROCESS FOR THE PRODUCTION OF STARCH DEGRADATION PRODUCTS WITH A NARROW MOLECULAR WEIGHT DISTRIBUTION

[75] Inventor: Ernst Nitsch, Linz, Austria

[73] Assignee: Laevosan-Gesellschaft mbH, Austria

[21] Appl. No.: 220,499

[22] Filed: Mar. 31, 1994

Related U.S. Application Data

[63] Continuation-in-part of PCT/EP92/02229, Sept. 28, 1992.

[30] Foreign Application Priority Data

Oct. 1, 1991 [DE] Germany ............ 4132701.2

[51] Int. Cl.$^6$ ............ A61K 31/70; C08B 30/12
[52] U.S. Cl. ............ 514/60; 435/99; 435/173.1; 536/80
[58] Field of Search ............ 536/56, 102, 80; 435/99, 173.1; 514/60

[56] References Cited

U.S. PATENT DOCUMENTS

| | | | |
|---|---|---|---|
| 3,436,309 | 4/1969 | Ottinger et al. | 435/99 |
| 3,632,475 | 1/1972 | Sugimoto et al. | 426/238 |
| 3,743,523 | 7/1973 | Bodine | 426/238 |
| 3,984,361 | 10/1976 | Gugliemelli et al. | 523/300 |
| 4,629,698 | 12/1986 | Nitsch et al. | 435/99 |
| 4,847,371 | 7/1989 | Schara et al. | 536/111 |
| 4,859,248 | 8/1989 | Thaler et al. | 536/45 |
| 5,114,509 | 5/1992 | Johnston et al. | 156/73.1 |

*Primary Examiner*—Herbert J. Lilling
*Attorney, Agent, or Firm*—Nikaido, Marmelstein, Murray & Oram

[57] ABSTRACT

A process is described for the production of starch degradation products with a narrow molecular weight distribution which is characterized in that a native starch, a starch derivative, a partially hydrolysed starch or a partially hydrolysed starch derivative in aqueous dispersion, suspension or solution is subjected to the action of ultrasound. Starch degradation products with a narrow molecular weight distribution can be obtained in high yields using this process.

16 Claims, 10 Drawing Sheets

PROCESS FOR THE PRODUCTION OF STARCH DEGRADATION PRODUCTS WITH A NARROW MOLECULAR WEIGHT DISTRIBUTION

CROSS REFERENCE TO RELATED APPLICATION

This application is a continuation-in-part of International application PCT/EP92/02229, filed Sep. 28, 1992, and designating the U.S.

DESCRIPTION

The invention concerns a process for the production of starch degradation products with a narrow molecular weight distribution.

Starch products are used nowadays for many applications in dietetics and medicine to achieve particular technological or physiological properties such as e.g. solubility, viscosity properties in solution, swelling and pasting properties, digestibility which are produced from native starches by partial degradation.

Common processes for this are heat and/or acid treatment in which so-called pyrodextrins or acid-modified starches are obtained (cf. O. B. Wurzburg, Modified Starches: Properties and Uses, CRC-Press Boca Raton, Fla., 1986, p. 18–38). A further method is the so-called mechanolytical degradation in which a reduction in molecular weight is achieved by dry vibration grinding (cf. Richter, Augustat, Schierbaum: "Ausgewählte Methoden der Stärkechemie, Wissenschaftliche Verlagsgesellschaft Stuttgard" 1968, p. 519–53). Although this is an elegant method, it has previously only been used on a laboratory scale and is hardly suitable for a technical scale.

Starches degraded either with acid (cf. U.S. Pat. No. 3,523,939) or with amylolytic enzymes (cf. DE-C 33 13 600) have previously been used for medical purposes such as e.g. as an intermediate product for the production of the plasma substitute hydroxethylstarch (HES). Pyrodextrins cannot be used for this since the native starch structure is substantially altered in these. In the degradation with acid as well as with enzymes, products are firstly formed with a very broad distribution of molecular weights from which the undesired low molecular components (glucose, maltose, oligosaccharides and polysaccharides up to ca. 30,000 Daltons) have to be removed before or after derivatization by precipitation with organic solvents such as e.g. acetone, by ultrafiltration or dialysis. Considerable reductions in yield occur naturally in this process (cf. the aforementioned patent applications). However, in all cases a final product is required with as narrow a distribution of molecular weight as possible and a defined average molecular weight which is usually stated as the weight average $\overline{M}_w$.

The object of the invention is therefore to create a process for the production of starch degradation products with a narrow molecular weight distribution with which the disadvantages described above and in particular undesired low molecular weight components can be largely avoided and with which an efficient degradation to form the desired products in high yields can be carried out.

This object is achieved according to the invention by a process for the production of starch degradation products with a narrow molecular weight distribution which is characterized in that a native starch, a starch derivative, a partially hydrolysed starch or a partially hydrolysed starch derivative in aqueous dispersion, suspension or solution is subjected to the action of ultrasound.

It was surprisingly found that an efficient degradation can be achieved by the treatment of aqueous dispersions, suspensions or solutions of starch with ultrasound.

It is possible according to the invention to adjust the desired average molecular weight (weight average $\overline{M}_w$) by varying the duration and intensity of the sonication to a desired magnitude with a very narrow molecular weight distribution and practical absence of undesired lower molecular components. In contrast to the previously known degradation methods, yields of almost 100 % can be achieved according to the invention.

According to the invention a suspension is understood as a dispersion of insoluble solid particles above colloidal dimensions and a solution is understood as a molecularly disperse dispersion of the starch starting products in water. A dispersion is also understood to include a gel.

It is possible according to the process of the invention to adjust the desired average molecular weight $\overline{M}_w$ within wide limits with a very narrow molecular weight distribution by carrying out the ultrasonic treatment for the time required to obtain the desired molecular weight independent of the other reaction conditions and in particular of the starting product.

The partially hydrolysed starch or partially hydrolysed starch derivative that is preferably used is a partial hydrolysate of starch or of a starch derivative obtained by acid hydrolysis and/or enzymatic hydrolysis and in particular one with an average molecular weight $\overline{M}_w$ of more than $10^6$ Daltons which is degraded to such an extent that a 10 to 40% solution can be readily pumped.

A starch is preferably used as the native starch which is mainly composed of amylopectin and in particular of almost amylose-free amylopectin which contains no more than 1% by weight amylose. Preferred examples of a starch used according to the invention are wax maize, wax rice and/or wax sorghum starch.

The production of a partially hydrolysed starch or of a partially hydrolysed starch derivative used as the starting product can be achieved in a well-known manner by means of acid hydrolysis or enzymatic hydrolysis. Hydrochloric acid is preferably used for the acid hydrolysis. α-Amylase is the preferred enzyme for the enzymatic hydrolysis.

Starch derivatives are for example hydroxyalkyl starch or alkoxyalkyl starch and in particular hydoxyethyl starch (HES).

In an embodiment of the invention, the reaction mixture obtained after the partial hydrolysis with acid or enzyme can also be used as a starting mixture which can then be subjected to ultrasonic treatment without previous isolation of the hydrolysate.

In practical embodiments of the invention one of the following are for example used: an aqueous 5 to 40% by weight dispersion of a native starch in gel form produced by forming a paste or an aqueous 5 to 40% by weight pumpable solution of a partially hydrolysed starch, or a 10 to 60% by weight suspension of a native starch, or a 10 to 50% by weight aqueous solution or dispersion of a high molecular (larger than 200,000 Daltons) starch derivative.

The ultrasonic treatment can be carried out in a well-known manner and with suitable commercially available equipment. The most suitable conditions for this depend in particular on the starch or starch derivative added as the starting product, the type of the initial reaction mixture (dispersion, suspension or solution) and the desired average molecular weight of the starch degradation product.

The processing is preferably carried out at room temperature or a slightly increased temperature and in particular in the temperature range of 20° C. to 80° C. wherein the temperature can also be decreased as the degradation progresses.

The ultrasonic treatment can be carried out batch wise or continuously. It is preferably carried out with a sonic dose in the range of 1 to 20 kWh/l depending on the desired degree of degradation.

It is expedient to carry out the ultrasonic treatment while stirring the reaction mixture.

The degree of degradation and thus the desired molecular weight of the starch degradation products can be easily monitored by measuring the viscosity of a sample diluted with water in order in this manner to determine the desired degradation and the end of the reaction. This also applies to the determination of the degree of hydrolysis of the partial hydrolysate used as the starting product.

The process according to the invention provides a process for the production of starch degradation products with a narrow molecular weight distribution wherein the desired degree of degradation can be obtained by suitable choice and variation of the intensity and/or duration of the sonication. Degradation products with a very narrow molecular weight distribution can be obtained according to the invention which, in contrast to previously known degradation methods, contain only very low proportions of undesired lower molecular components.

BRIEF DESCRIPTION OF DRAWINGS

FIG. 4 is molecular weight distribution of starch degradation products in suspension as disclosed in Example 2. FIG. 5 is the molecular weight distribution of HES before degradation. FIG. 6 is the molecular weight distribution of HES after degradation as disclosed in Example 3. FIG. 7 is the molecular weight distribution as determined by gel chromatography after the complete sonication for a sonic power of 250 W. FIG. 8 is the molecular weight distribution as determined by gel chromatography after the complete sonication for a sonic power of 150 W. FIG. 9 is the molecular weight distribution as determined by gel chromatography after the complete sonication for a sonic power of 30 W. FIG. 10 illustrates the degradation of enzymatic pre-degraded wax maize starch using ultrasound as monitored by the measurement of the average molecular weight against time for the degradation products as disclosed in Example 5.

The process according to the invention is therefore particularly suitable for the production of starting materials or final products of starch derivatives such as e.g. starch ethers (e.g. hydroxyethyl starch) or starch esters (e.g. acetyl starch) in high yield which are used medically e.g. for clinical and preferably parenteral applications. The starch degradation products obtained according to the invention are particularly suitable as starting products for the production of pharmaceutical compositions for peritoneal dialysis as well as for the production of blood plasma substitutes in the form of for example starch ethers or starch esters.

The invention therefore also concerns the use of starch degradation products obtained by the process according to the invention for pharmaceutical compositions for clinical and preferably parenteral applications and in particular for the production of pharmaceutical compositions for peritoneal dialysis as well as for the production of blood plasma substitutes.

Depending on the intended use of the starch degradation products according to the invention it may also be expedient to largely remove salts and other low molecular components such as e.g. lower molecular degradation products of the original starch which may still be present. This can for example be achieved by dialysis and in particular by ultrafiltration (diafiltration) in which membranes with an appropriate exclusion limit can be selected depending on the intended use. It is expedient to remove the lower molecular components together with the salts.

In order to improve the handling and storage stability of the starch degradation products according to the invention it may also be expedient to convert the products obtained after treatment with ultrasound into a dry product. This is preferably carried out by a mild concentration of the solution in a vacuum and subsequently drying in a vacuum. However, it is also possible to convert the reaction mixture by lyophilization into a freeze-dried product.

The following examples are intended to elucidate the invention in more detail without being limited thereto.

$\overline{M}_w$ denotes weight average and $\overline{M}_n$ denotes number average. Details of temperature refer to the Celsius scale.

EXAMPLES

Example 1

Figure 1:
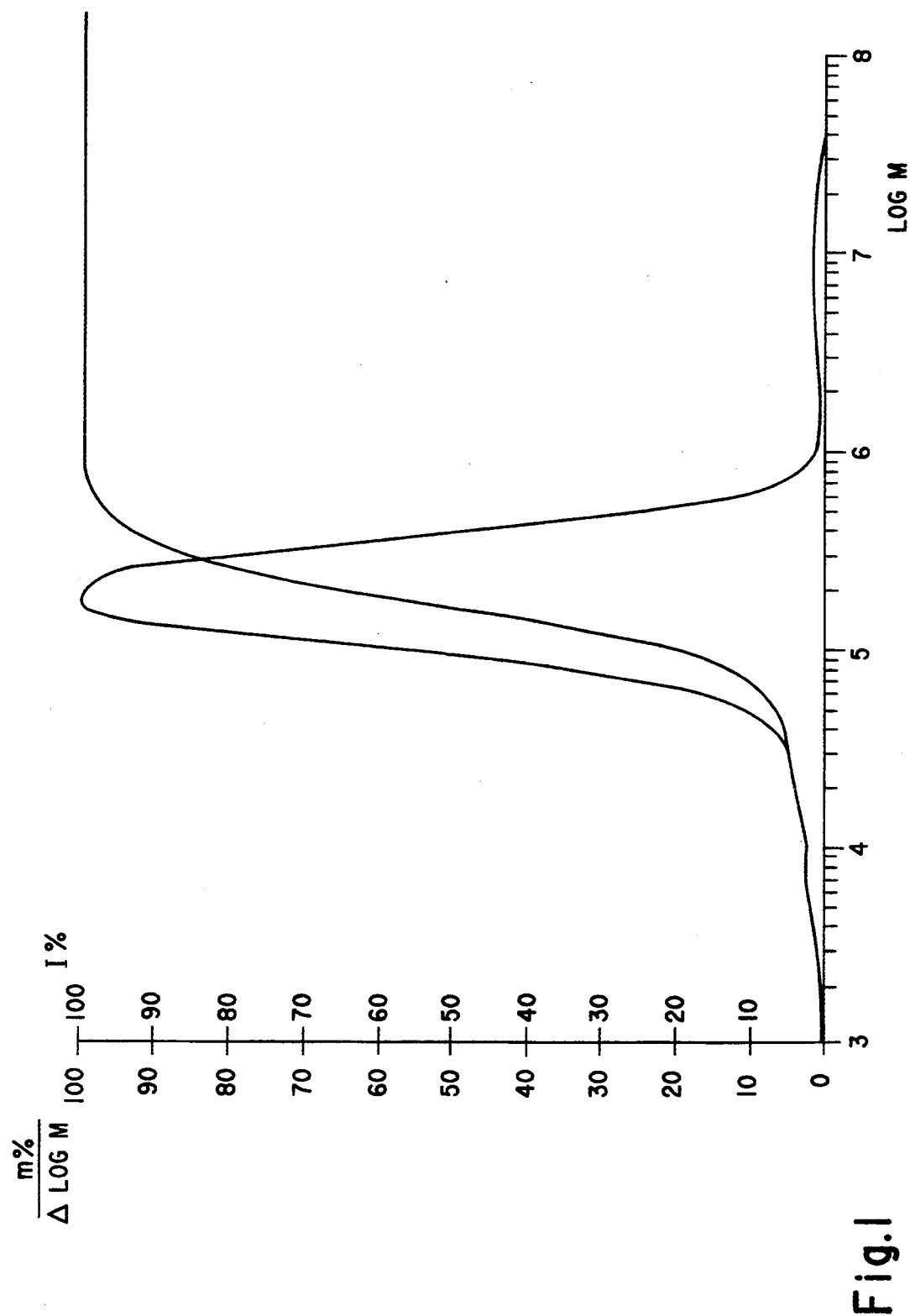
FIGS. 1 to 3 show the integral and differential molecular weight distribution of starch degradation products produced according to the invention (FIG. 1) and of starch degradation products produced by acid hydrolysis (FIG. 2) and by enzymatic hydrolysis (FIG. 3); this clearly shows the considerably narrower molecular weight distribution obtained by the process according to the invention.

A gel of 1 g wax maize starch produced by forming a paste at 100° C. and 19 g distilled water were placed in a beaker of 30 mm diameter. The standard probe of a 20 kHz ultrasonic homogenizer LABSONIC U from the BRAUN Melsungen Company, tip diameter 19 mm, was immersed about 17 mm into the gel filling. The sonication was carried out while cooling with ice water at a power of 250 watts and a cycle time of 0.7 seconds. The effective sonic dose was 17.5 kWh/l. Liquefaction occurred after a few minutes. After a total of 2 hours the experiment was terminated and the molecular weight distribution of the solution which was now fluid was determined by gel chromatography using hydroxyethyl starch standards (cf. FIG. 1).

The molecular weight averages calculated from this were:

$\overline{M}_w = 231\ 800$
$\overline{M}_n = 54\ 400$

The proportion <50.000 Daltons was 6.2%.

Figure 2:
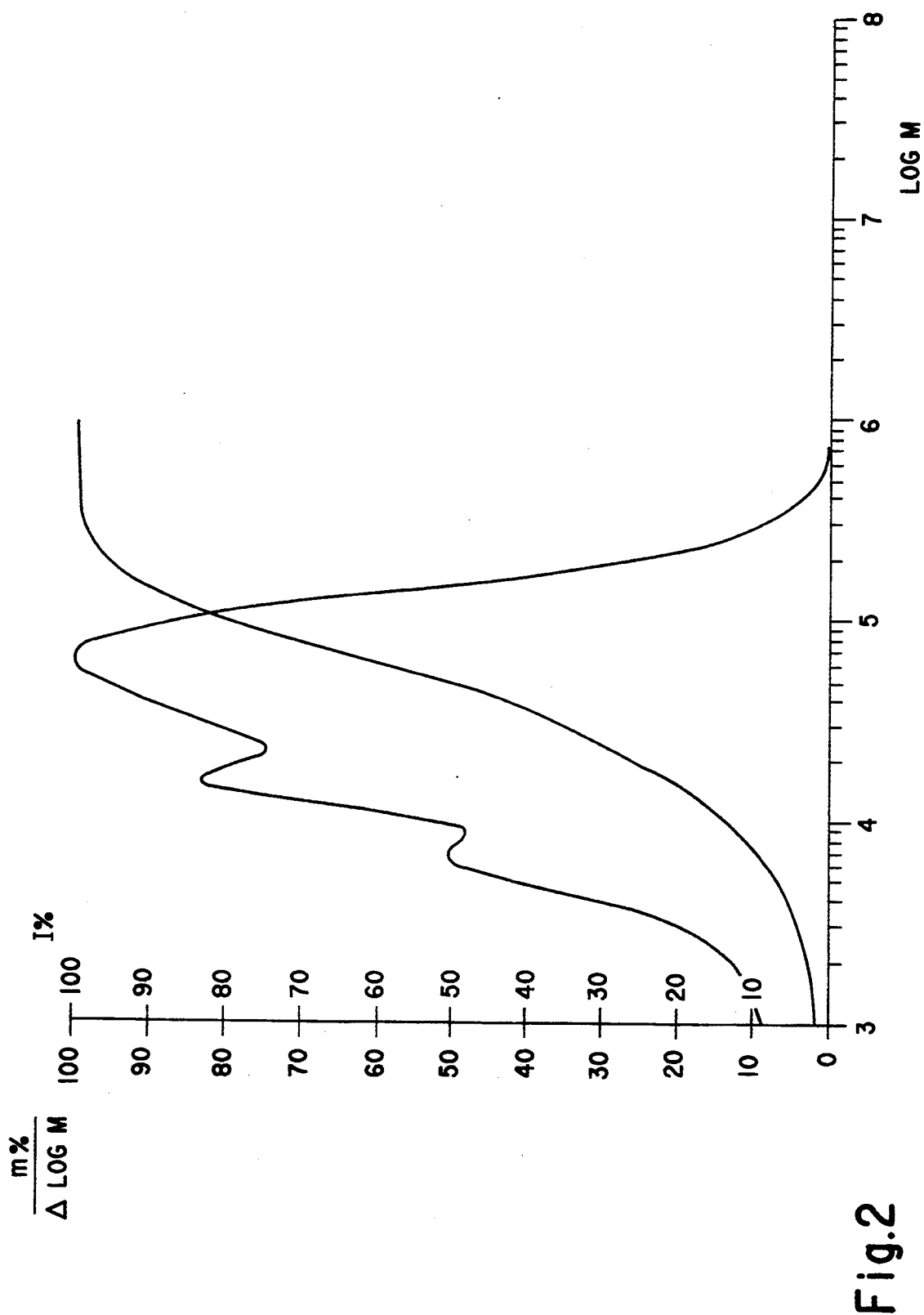

Comparative example 1 (acid hydrolysis 5 g wax maize starch was suspended in 100 ml 0.01 M hydrochloric acid, a paste was formed by heating in a boiling water bath while stirring and it was kept at the water bath temperature for a further 5 hours. The solution which was now fluid was then deacidified by filtration over a weakly basic anion exchanger in the OH⁻ form (LEWATIT AP 49 from the BAYER Leverkusen Company) and the molecular weight distribution was determined as in example 1 (cf. FIG. 2).

The molecular weight averages calculated from this were:
$\overline{M}_w = 62700$
$\overline{M}_n = 3000$
The proportion <50.000 Daltons was 51.5%.

The considerably lower averages in comparison to example 1 are in this case the result of the considerably higher proportion of lower molecular components whereas the degree of degradation of the high molecular components >30.000 Daltons is approximately comparable.

Comparative example 2 (enzymatic hydrolysis)

Figure 3:
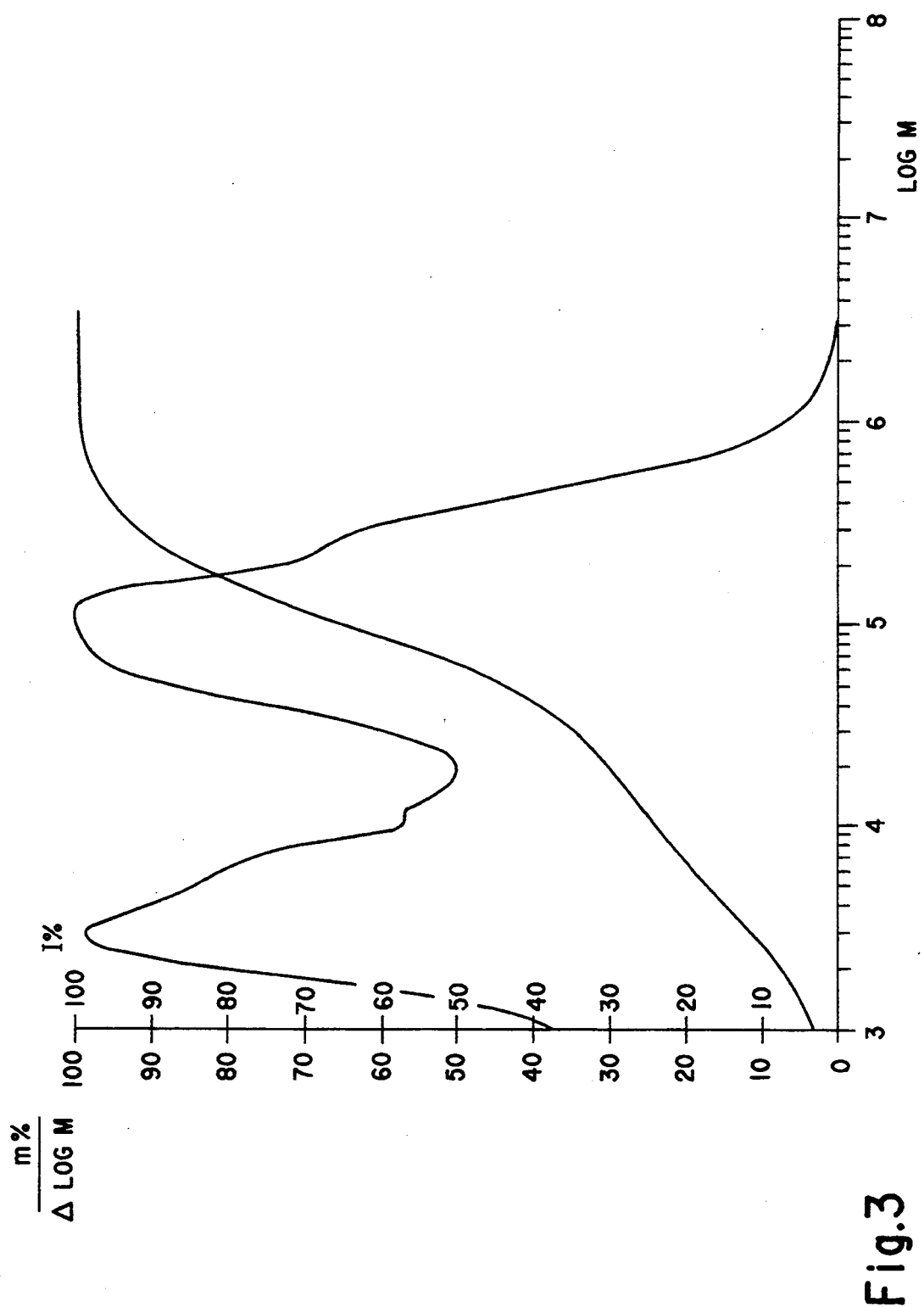

35 g wax maize starch was suspended in 100 ml of an aqueous solution containing 0.02 g calcium chloride-2-H₂O and 0.02 ml α-amylase (TERMAMYL from the NOVO Company, Copenhagen) and heated in a boiling water bath while stirring vigorously. Dissolution occurred at about 65° C. without formation of a highly viscous phase. It was kept at water bath temperature for 1 hour, adjusted to pH 3.0 with hydrochloric acid in order to inactivate the enzyme and cooled. The molecular weight distribution was determined as described in example 1 (cf. FIG. 3).

The molecular weight averages calculated from this were:
$\overline{M}_w = 103500$
$\overline{M}_n = 5800$
The proportion <50,000 Daltons was 45%.

Example 2

Starch degradation in suspension

Figure 4:
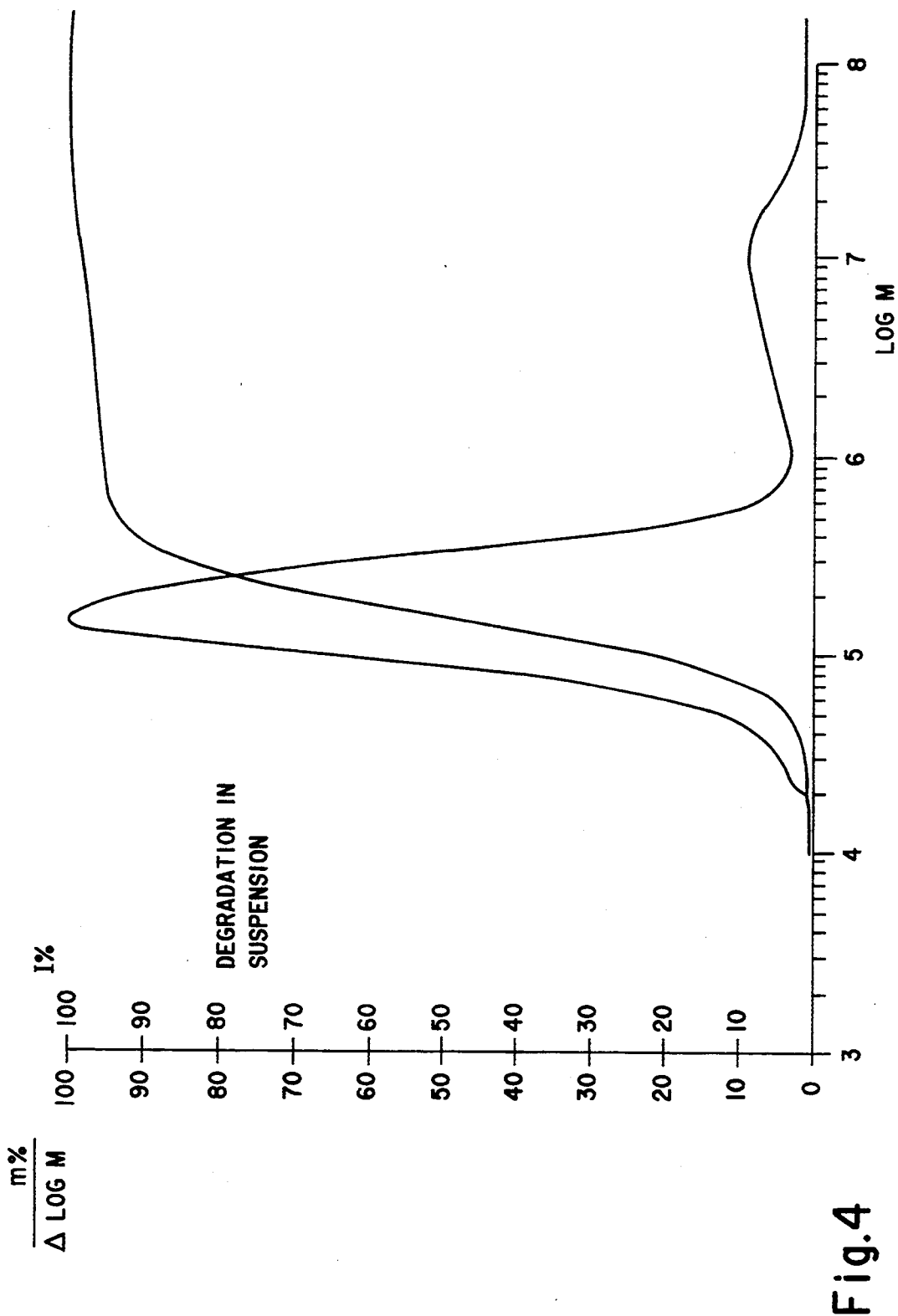
FIGS. 4–10 are plots of data discussed in the Examples reported herein.

A suspension of 1 g wax maize starch in 19 g distilled water was used and treated with the same sonic dose and using the same arrangement as in experiment 1. Microscopic examination of the macroscopically unchanged suspension after sonication showed a considerable particle degradation of the starch. After heating to 100° C. a solution of relatively low viscosity was obtained. The following molecular weight values were determined by gel chromatography (s. FIG. 4):
$\overline{M}_w = 691800$
$\overline{M}_n = 134600$
The proportion <50,000 Daltons was 2.78%.

Example 3

Degradation of hydroxyethyl starch (HES)

Figure 5:
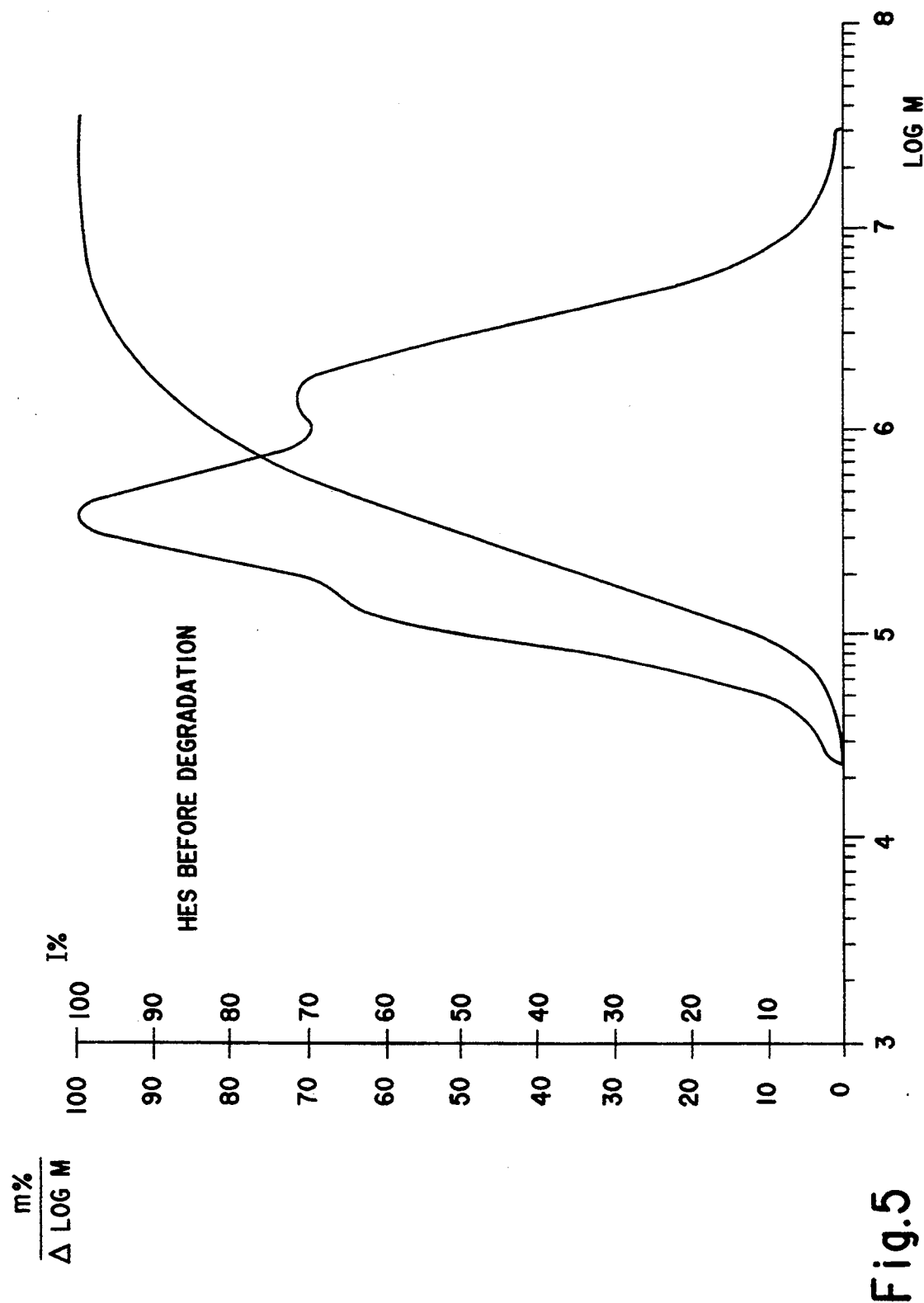

50 ml of a solution containing 10 g HES $\overline{M}_w$ 739,100, $\overline{M}_n$ 219,300 (cf. FIG. 5 for molecular weight distribution), molar substitution 0.7 mol hydroxyethyl groups/mol anhydroglucose, was placed in a 50 ml wide-neck infusion bottle, inside diameter 37 mm, and sonicated as in example 1 with a sonication power of 250 watts while cooling with ice water.

Figure 6:
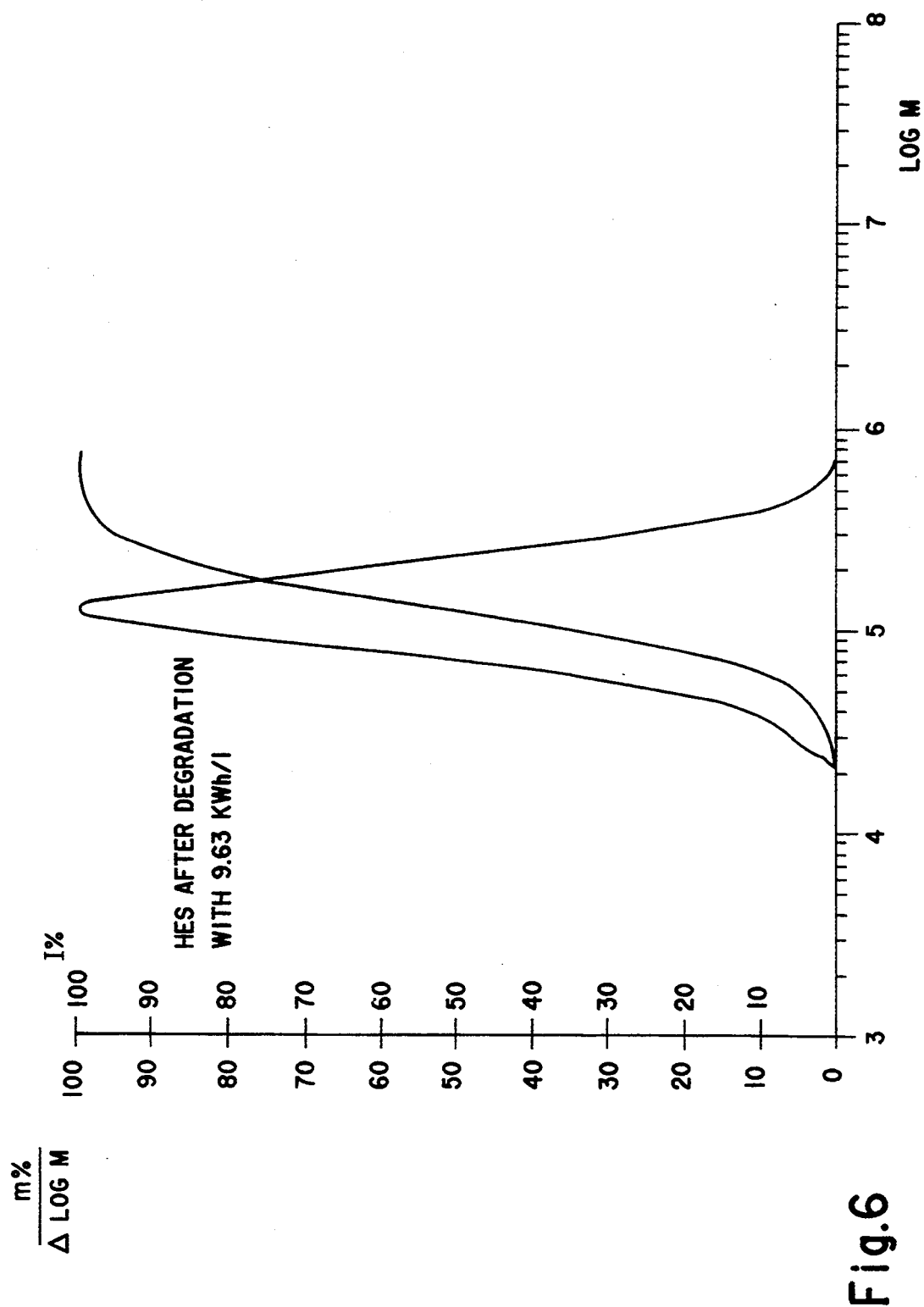

The progress of the degradation was monitored by measuring the relative viscosity $n_{rel}$ of a 20% solution. After the complete sonication period the molecular weight distribution was determined by gel chromatography (FIG. 6).

TABLE

| Sonic dose KWh/l | $n_{rel}$ |
|---|---|
| 0 | 10.70 |
| 1.75 | 7.51 |
| 4.38 | 4.82 |
| 7.0 | 4.04 |
| 9.36 | 3.62 |
| $\overline{M}_w = 132700$ | |
| $\overline{M}_n = 103300$ | |
| The proportion < 50,000 Daltons was 4.8%. | |

Example 4

Dependence of starch gel degradation on sonic power and sonic dose 10 g wax maize starch suspended in water to a volume of 50 ml was placed in a 50 ml wide-neck infusion bottle, inside diameter 37 mm, and made into a paste by placing it in a boiling water bath while stirring and sonicated as in example 3 while cooling with ice water.

Sonic power:
a) 250 W
b) 150 W
c) 30 W

The progress of the degradation with time was monitored in each case by measuring the relative viscosity $n_{rel}$ of a 20% solution. After the complete sonication period the molecular weight distribution was determined by gel chromatography.

TABLE

Figure 7:
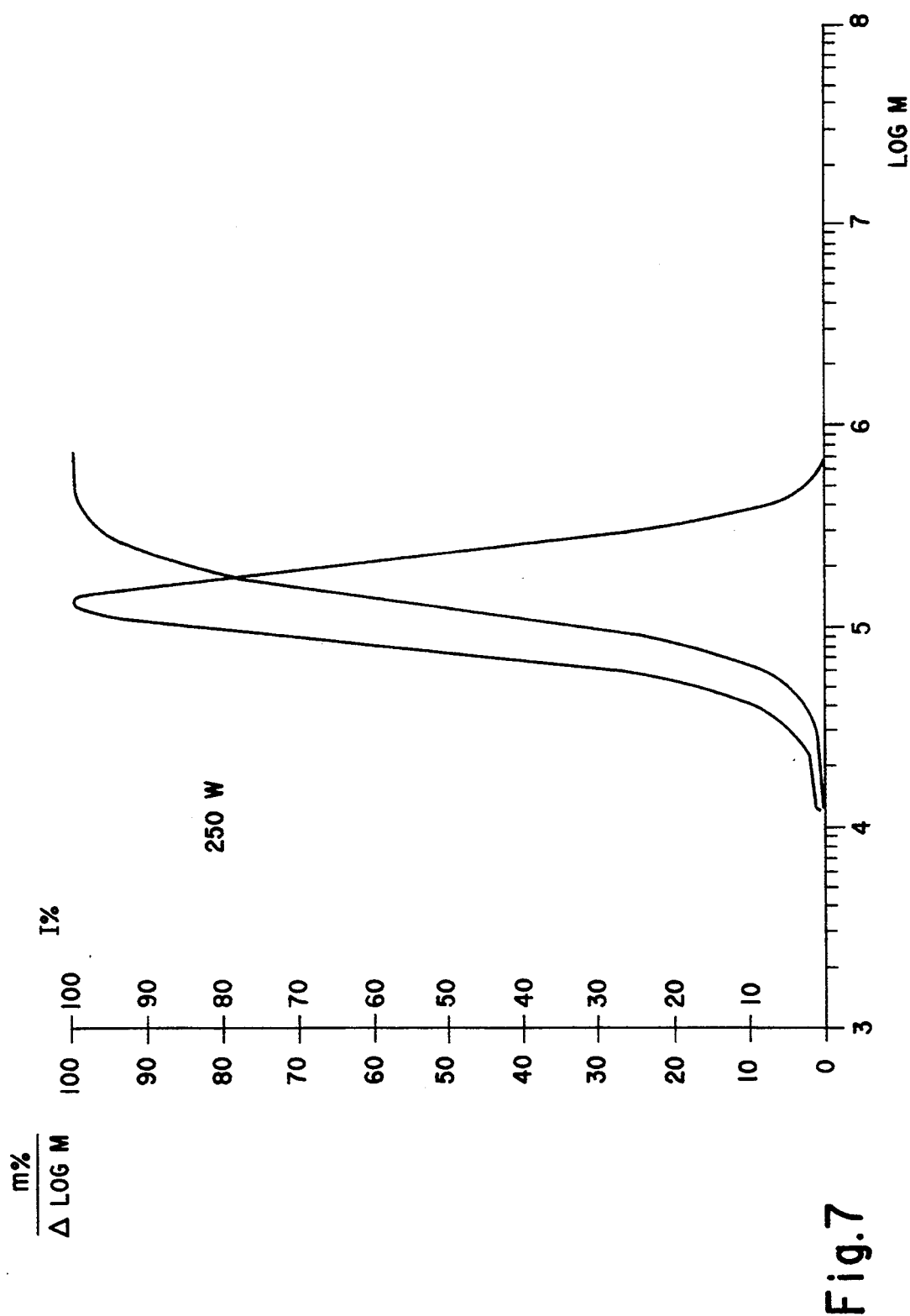
Figure 8:
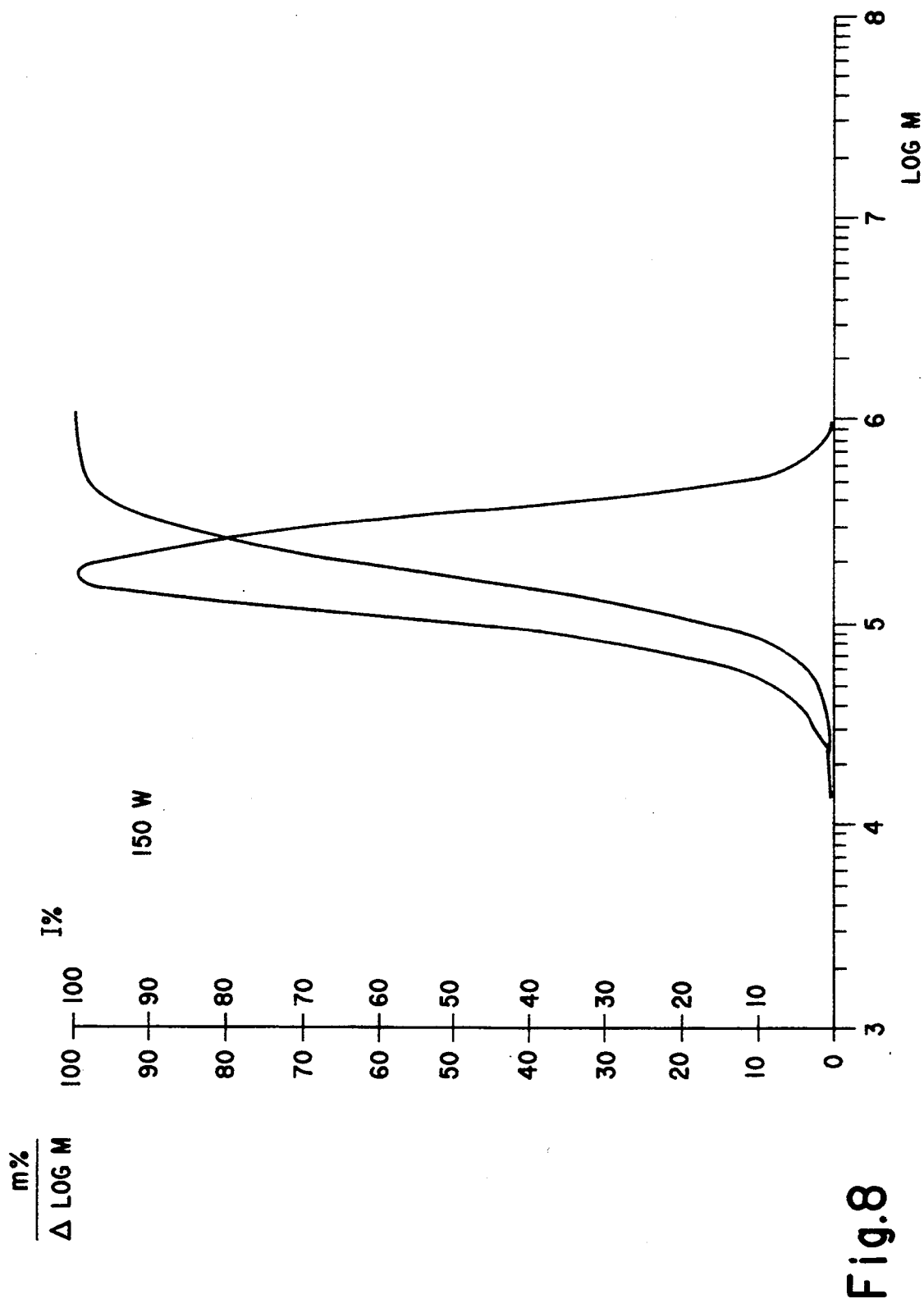
Figure 9:
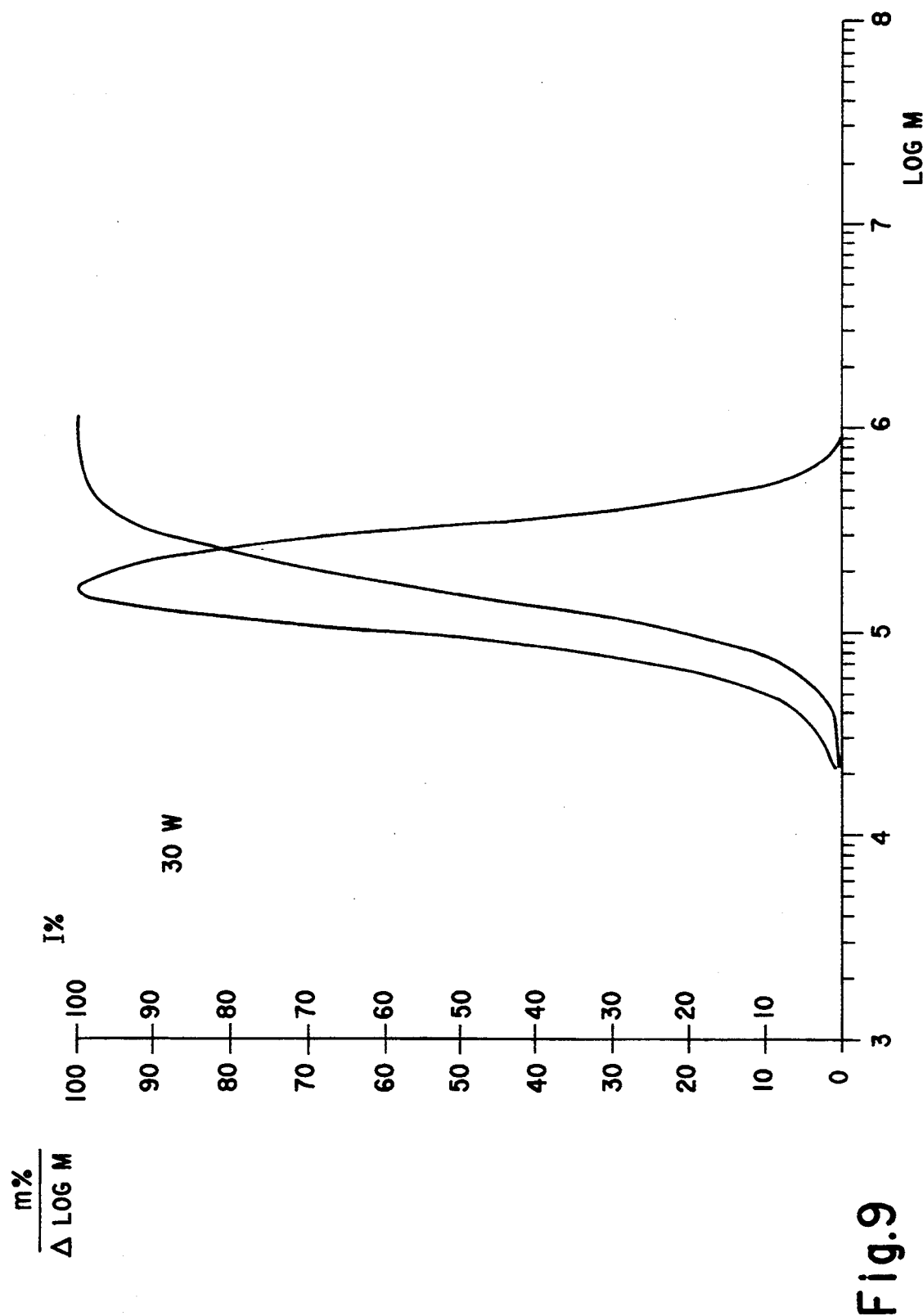

| Time (min) | Sonic dose KWh/l | $n_{rel}$ |
|---|---|---|
| a) 250 W | | |
| 30 | 1.75 | 8.3 |
| 60 | 3.50 | 5.6 |
| 90 | 5.25 | 4.4 |
| 120 | 7.0 | 3.6 |
| 150 | 8.75 | 3.2 |
| 165 | 9.63 | 3.2 |
| FIG. 7 | | |
| $\overline{M}_w = 141000$ | | |
| $M_n = 109100$ | | |
| The proportion < 50000 Daltons was 4.08%. | | |
| b) 150 W | | |
| 30 | 1.05 | 12.0 |
| 60 | 2.10 | 8.1 |
| 90 | 3.15 | 5.8 |
| 120 | 4.20 | 5.2 |
| 150 | 5.25 | 4.6 |
| 165 | 5.78 | 4.5 |
| FIG. 8 | | |
| $\overline{M}_w = 180,700$ | | |
| $M_n = 137,700$ | | |
| The proportion < 50000 Daltons was 2.01%. | | |
| c) 30 W | | |
| 30 | 0.21 | not measurable |
| 60 | 0.42 | not measurable |
| 90 | 0.63 | 5.9 |
| 120 | 0.84 | 5.2 |
| 150 | 1.05 | 4.6 |
| 165 | 1.16 | 4.5 |
| FIG. 9 | | |
| $\overline{M}_w = 1799000$ | | |
| $M_n = 137200$ | | |
| The proportion < 50000 Daltons was 1.98% | | |

Example 5

Degradation of enzymatically liquefied starch 35 g wax maize starch was suspended in 100 ml water in a beaker, 20 μl α-amylase Termamyl (NOVO Co.

Copenhagen) was added and it was heated in a water bath while stirring until the starch particles had completely dissolved and a viscous solution had formed. The enzyme was stopped by acidification with ca. 50 μl conc. hydrochloric acid to pH 2.80.

The starch partial hydrolysate obtained was sonicated with a sonic power of 250 W in a 100 ml wide-neck infusion bottle while cooling with ice water and the progress of the degradation with time was monitored by measuring the relative viscosity $n_{rel}$ of a 20% solution and the molecular weight distribution.

TABLE

| Time min | Sonic dose KWh/l | $n_{rel}$ | $\overline{M}_w^* \cdot 10^{-3}$ | $\overline{M}_n \cdot 10^{-3}$ | <50000 D % |
|---|---|---|---|---|---|
| 0 | 0 | 95 | 4178 | 4.16 | 6.57 |
| 30 | 0.65 | 21.2 | 721.5 | 64.5 | 6.13 |
| 60 | 1.30 | 13.8 | 431.7 | 74.5 | 5.85 |
| 120 | 2.59 | 10.0 | 230.2 | 62.5 | 6.63 |
| 180 | 3.89 | 8.3 | 175.4 | 62.1 | 7.33 |
| 240 | 5.19 | 7.2 | 138.6 | 49.7 | 9.09 |

Figure 10:
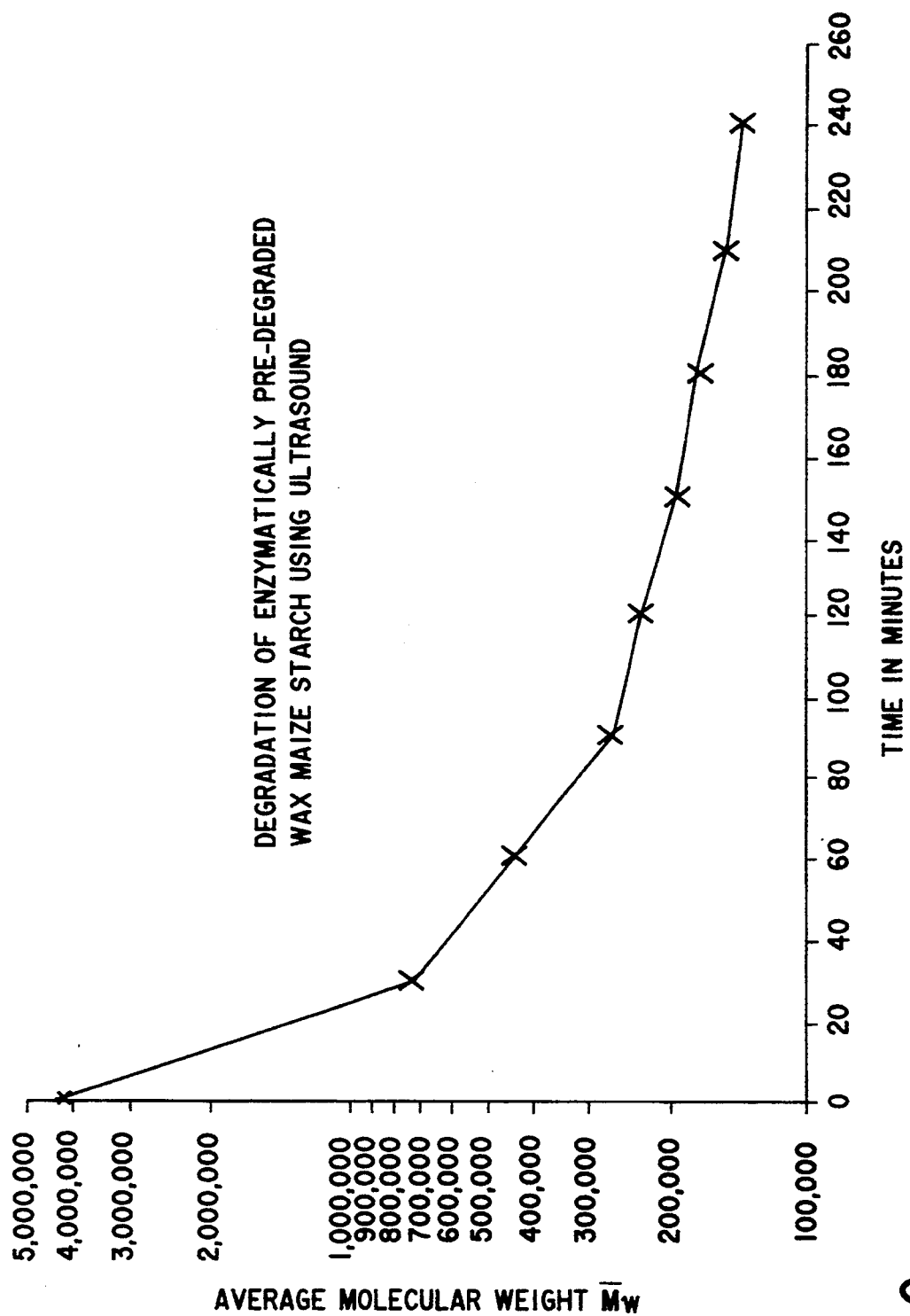

*see FIG. 10

I claim:

1. Process for the production of starch degradation products with a narrow molecular weight distribution, wherein a native starch, a starch derivative, a partially hydrolysed starch or a partially hydrolysed starch derivative in aqueous dispersion, suspension or solution is subjected to the action of ultrasound in which it is degraded with sonic doses of 1–20 kWh/l to a ratio of weight average molecular ($\overline{M}_w$) to number average molecular weight ($\overline{M}_n$) of 1.3–5.8 and the proportion of degradation products with a molecular weight of <50,000 Daltons is less than 10%.

2. Process as claimed in claim 1, wherein the ultrasound treatment is carried out until the desired average molecular weight $\overline{M}_w$ has been obtained.

3. Process as claimed in claim 1, wherein a partial hydrolysate of starch or of a starch derivative obtained by acid hydrolysis and/or enzymatic hydrolysis is used as the partially hydrolysed starch or partially hydrolysed starch derivative 4. Process as claimed in claim 3, wherein a starch or starch derivative partially hydrolysed to an average molecular weight of more than $10^6$ Daltons is used.

5. Process as claimed in claim 1, wherein a gel-like aqueous dispersion of a native starch produced by forming a paste is used.

6. Process as claimed in claim 1, wherein a 5 to 40% by weight pumpable aqueous dispersion of a partially hydrolysed starch or of a partially hydrolysed starch derivative is used.

7. Process as claimed in claim 1, wherein a 10 to 60% by weight suspension of a native starch is used.

8. Process as claimed in claim 1, wherein a 10 to 50% by weight aqueous solution or dispersion of a starch derivative is used.

9. Process as claimed in claim 1, wherein a native starch is used which does not contain more than 1% by weight amylose.

10. Process as claimed in claim 9, wherein wax maize, wax rice and/or wax sorghum starch is used.

11. Process as claimed in claim 1, wherein the partially hydrolysed starch or the partially hydrolysed starch derivative is obtained by acid hydrolysis and/or enzymatic hydrolysis.

12. Process as claimed in claim 11, wherein α-amylase is used as the enzyme.

13. Process as claimed in claim 1, wherein the reaction mixture obtained after partial hydrolysis is subjected to ultrasonic treatment without previous isolation of the hydrolysate.

14. Process as claimed in claim 1, wherein hydroxyethyl starch is used as the starch derivative.

15. A method of producing a pharmaceutical composition, comprising mixing a starch degradation product obtained according to the process as claimed in claim 1 with a pharmaceutically acceptable carrier or excipient.

16. A method as claimed in claim 15, wherein said pharmaceutical composition is suitable for peritoneal dialysis and for producing blood plasma substitutes.

* * * * *